US012622647B2

(12) United States Patent
Min et al.

(10) Patent No.: US 12,622,647 B2
(45) Date of Patent: May 12, 2026

(54) RUNTIME ASSESSMENT OF SENSORS

(71) Applicant: Nokia Technologies Oy, Espoo (FI)

(72) Inventors: Chulhong Min, Cambridge (GB); Alessandro Montanari, Cambridge (GB); Fahim Kawsar, Cambridge (GB); Akhil Mathur, London (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 536 days.

(21) Appl. No.: 17/760,629

(22) PCT Filed: Aug. 31, 2020

(86) PCT No.: PCT/IB2020/058107
§ 371 (c)(1),
(2) Date: Mar. 15, 2022

(87) PCT Pub. No.: WO2021/053444
PCT Pub. Date: Mar. 25, 2021

(65) Prior Publication Data
US 2022/0330896 A1 Oct. 20, 2022

Related U.S. Application Data

(60) Provisional application No. 62/903,565, filed on Sep. 20, 2019.

(51) Int. Cl.
*A61B 5/00* (2006.01)
*G06N 3/08* (2023.01)
(52) U.S. Cl.
CPC .......... *A61B 5/7221* (2013.01); *A61B 5/7267* (2013.01); *G06N 3/08* (2013.01)
(58) Field of Classification Search
CPC ..... A61B 5/7221; A61B 5/7267; A61B 5/681; A61B 5/6898; A61B 5/0024;
(Continued)

(56) References Cited

U.S. PATENT DOCUMENTS 5,898,304 A 4/1999 Mandl
6,675,031 B1 * 1/2004 Porges ................. A61B 5/7221
600/330
(Continued)

FOREIGN PATENT DOCUMENTS

CN 101867960 A 10/2010
CN 106108917 A 11/2016
(Continued)

OTHER PUBLICATIONS

Office action received for corresponding European Patent Application No. 20768109.9, dated Feb. 7, 2024, 4 pages.
(Continued)

*Primary Examiner* — Catherine T. Rastovski
*Assistant Examiner* — Yossef Korang-Beheshti
(74) *Attorney, Agent, or Firm* — DITTHAVONG, STEINER & MLOTKOWSKI

(57) ABSTRACT

This relates to the use of sensor evaluation in a multi-sensor environment. In a first aspect, this specification describes apparatus comprising: at least one processor; and at least one memory including computer program code. The at least one memory and the computer program code are configured to, with the at least one processor, cause the apparatus at least to perform: receive sensor data from a plurality of sensors collected during a first time period; process the received sensor data through a plurality of layers of a neural network to generate an output indicative of the sensing quality of each of the plurality of sensors for a task; and cause a subset of the plurality of sensors to collect data during a second time period based on the output indicative of the suitability of each of the plurality of sensors for the task.

19 Claims, 11 Drawing Sheets

(58) Field of Classification Search

CPC ........ A61B 5/1118; A61B 5/165; G06N 3/08; G06N 7/01; G06N 20/10; G06N 3/045; G01D 21/00; G01D 3/08; G01D 21/02; G06F 18/211

See application file for complete search history.

(56) References Cited

U.S. PATENT DOCUMENTS

| | | | |
|---|---|---|---|
| 8,478,306 | B2 | 7/2013 | Zheng |
| 8,599,710 | B2 | 12/2013 | Song et al. |
| 9,053,706 | B2 | 6/2015 | Jitkoff et al. |
| 9,712,629 | B2 | 7/2017 | Molettiere et al. |
| 2009/0002148 | A1 | 1/2009 | Horvitz |
| 2014/0156228 | A1 | 6/2014 | Molettiere et al. |
| 2017/0010658 | A1 | 1/2017 | Tanaka et al. |
| 2018/0018585 | A1 | 1/2018 | Marin et al. |
| 2018/0183661 | A1* | 6/2018 | Wouhaybi .............. G01D 18/00 |
| 2018/0322263 | A1 | 11/2018 | Hallock |
| 2018/0367560 | A1 | 12/2018 | Mahaffey et al. |
| 2019/0175115 | A1* | 6/2019 | Patel ...................... A61B 5/721 |
| 2019/0205744 | A1 | 7/2019 | Mondello et al. |
| 2020/0090045 | A1* | 3/2020 | Baker .................... G06N 3/084 |
| 2021/0117787 | A1* | 4/2021 | Stal ........................... G06N 3/04 |
| 2021/0382441 | A1* | 12/2021 | Rakshit ................ G04G 17/045 |
| 2022/0036126 | A1* | 2/2022 | Gaidon .................. G06V 20/56 |

FOREIGN PATENT DOCUMENTS

| | | | | |
|---|---|---|---|---|
| CN | 106596754 | A | | 4/2017 |
| CN | 109863488 | A | | 6/2019 |
| CN | 111382679 | A | * | 7/2020 ......... G06K 9/00348 |
| JP | H1049509 | A | * | 2/1998 |

OTHER PUBLICATIONS

Safaei et al., "Reliability side-effects in internet of things application layer protocols", 2nd International Conference on System Reliability and Safety (ICSRS), Dec. 20-22, 2017, pp. 207-212.

Zappi et al., "Activity recognition from on-body sensors: accuracy-power trade-off by dynamic sensor selection", European Conference on Wireless Sensor Networks, 2008, pp. 17-33.

Kang et al., "Seemon: scalable and energy-efficient context monitoring framework for sensor-rich mobile environments", Proceedings of the 6th international conference on Mobile systems, applications, and services, Jun. 2008, pp. 267-280.

Kang et al., "Orchestrator: An active resource orchestration framework for mobile context monitoring in sensor-rich mobile environments", IEEE International Conference on Pervasive Computing and Communications (PerCom), Mar. 29-Apr. 2, 2010, pp. 135-144.

Keally et al., "Pbn: towards practical activity recognition using smartphone-based body sensor networks", Proceedings of the 9th ACM Conference on Embedded Networked Sensor Systems, Nov. 2011, pp. 246-259.

Melekhov et al., "Siamese network features for image matching", 23rd International Conference on Pattern Recognition (ICPR), Dec. 4-8, 2016, pp. 378-383.

Guo et al., "On calibration of modern neural networks", Proceedings of the 34th International Conference on Machine Learning, 2017, 10 pages.

Zadrozny et al., "Obtaining calibrated probability estimates from decision trees and naive Bayesian classifiers", Proceedings of the Eighteenth International Conference on Machine Learning, Jun. 2001, 8 pages.

Zadrozny et al., "Transforming classifier scores into accurate multiclass probability estimates", Proceedings of the eighth ACM SIGKDD international conference on Knowledge discovery and data mining, Jul. 2002, pp. 694-699.

Naeini et al., "Obtaining well calibrated probabilities using bayesian binning", Proceedings of the Twenty-Ninth AAAI Conference on Artificial Intelligence, Jan. 2015, pp. 2901-2907.

Platt, "Probabilistic outputs for support vector machines and comparisons to regularized likelihood methods", Advances in Large Margin Classifiers, Mar. 26, 1999, pp. 1-11.

Mizil et al., "Predicting good probabilities with supervised learning", Proceedings of the 22nd international conference on Machine learning, Aug. 2005, pp. 625-632.

Scheffer et al., "Active hidden markov models for information extraction", International Symposium on Intelligent Data Analysis, 2001, pp. 309-318.

Shannon, "A mathematical theory of communication", The Bell System Technical Journal, vol. 27, 1948, pp. 1-55.

Körner et al., "Multi-class ensemble-based active learning", Proceedings of the 17th European conference on Machine Learning, Sep. 2006, pp. 687-694.

Pan et al., "A survey on transfer learning", IEEE Transactions on Knowledge and Data Engineering, vol. 22, No. 10, Oct. 2010, pp. 1345-1359.

"About Opportunity", Opportunity, Retrieved on Mar. 4, 2022, Webpage available at : http://www.opportunity-project.eu/.

Lee et al., "CoMon+: A Cooperative Context Monitoring System for Multi-Device Personal Sensing Environments", IEEE Transactions on Mobile Computing, vol. 15, No. 8, Aug. 1, 2016, pp. 1908-1924.

Guo et al., "Context-Aware Scheduling in Personal Data Collection From Multiple Wearable Devices", IEEE Access, vol. 5, Feb. 8, 2017, pp. 2602-2614.

Li et al., "Answering the Min-Cost Quality-Aware Query on Multi-Sources in SensorCloud Systems †", Sensors, vol. 18, No. 12, 2018, pp. 1-15.

Min et al., "A Closer Look at Quality-Aware Runtime Assessment of Sensing Models in Multi-Device Environments", Proceedings of the 17th Conference on Embedded Networked Sensor Systems, Nov. 2019, pp. 271-284.

International Search Report and Written Opinion received for corresponding Patent Cooperation Treaty Application No. PCT/IB2020/058107, dated Dec. 14, 2020, 12 pages.

Xu et al., "Integrated sensor array optimization with statistical evaluation", Sensors and Actuators B: Chemical, vol. 149, No. 1, Aug. 6, 2010, pp. 239-244.

Office Action for related Chinese Patent Application No. 2020800648658, dated Jun. 14, 2024, 25 pages.

Office Action for related Chinese Patent Application No. 2020800648658, dated Nov. 15, 2024, 25 pages.

Office Action for related Chinese Application No. 202080064865.8, dated Feb. 12, 2025, 23 pages.

Office Action for related European Application No. 20 768 109.9-1001, dated Jul. 8, 2025, 48 pages.

* cited by examiner

200

Heuristic Approach

| Sense | SM | Tx<br>Confidence<br>(10B/sec) | | Idle | |
| Sense | SM | HOA | | Idle | |
| Sense | SM | Tx<br>Confidence<br>(10B/sec) | Sense | SM | Sense | SM |

Learning Approach

| Sense | Tx<br>Raw data<br>(200B/sec) | | Idle | |
| Sense | LOA | | Idle | |
| Sense | Tx<br>Raw data<br>(200B/sec) | Sense | SM | Sense | SM | Sense | SM |

204    214    214    208    206b    206a

Assessment
Window

Execution Window with
Selected Device

202    Execution Duty Cycle    212    210

300

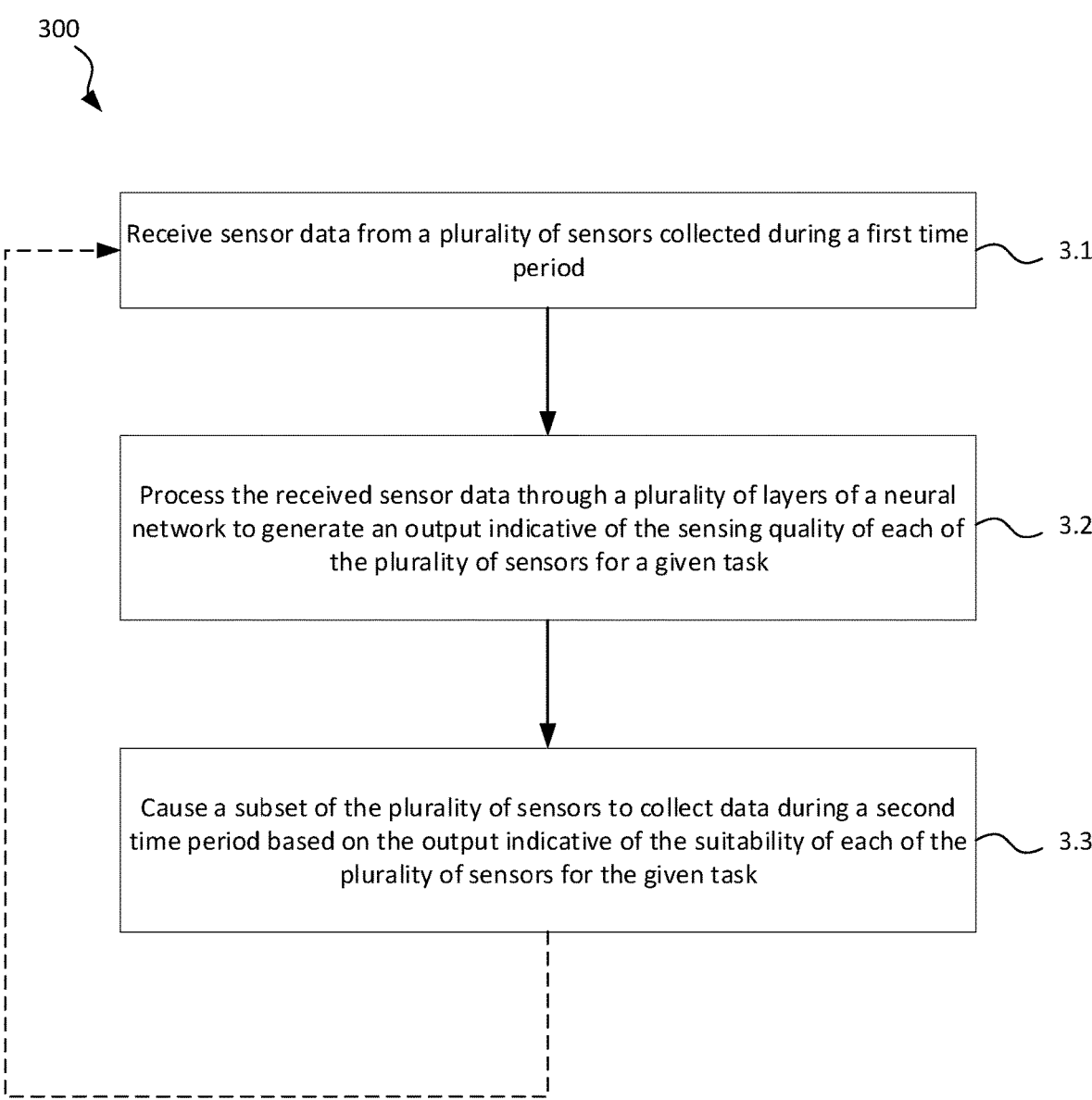

Receive sensor data from a plurality of sensors collected during a first time period — 3.1

Process the received sensor data through a plurality of layers of a neural network to generate an output indicative of the sensing quality of each of the plurality of sensors for a given task — 3.2

Cause a subset of the plurality of sensors to collect data during a second time period based on the output indicative of the suitability of each of the plurality of sensors for the given task — 3.3

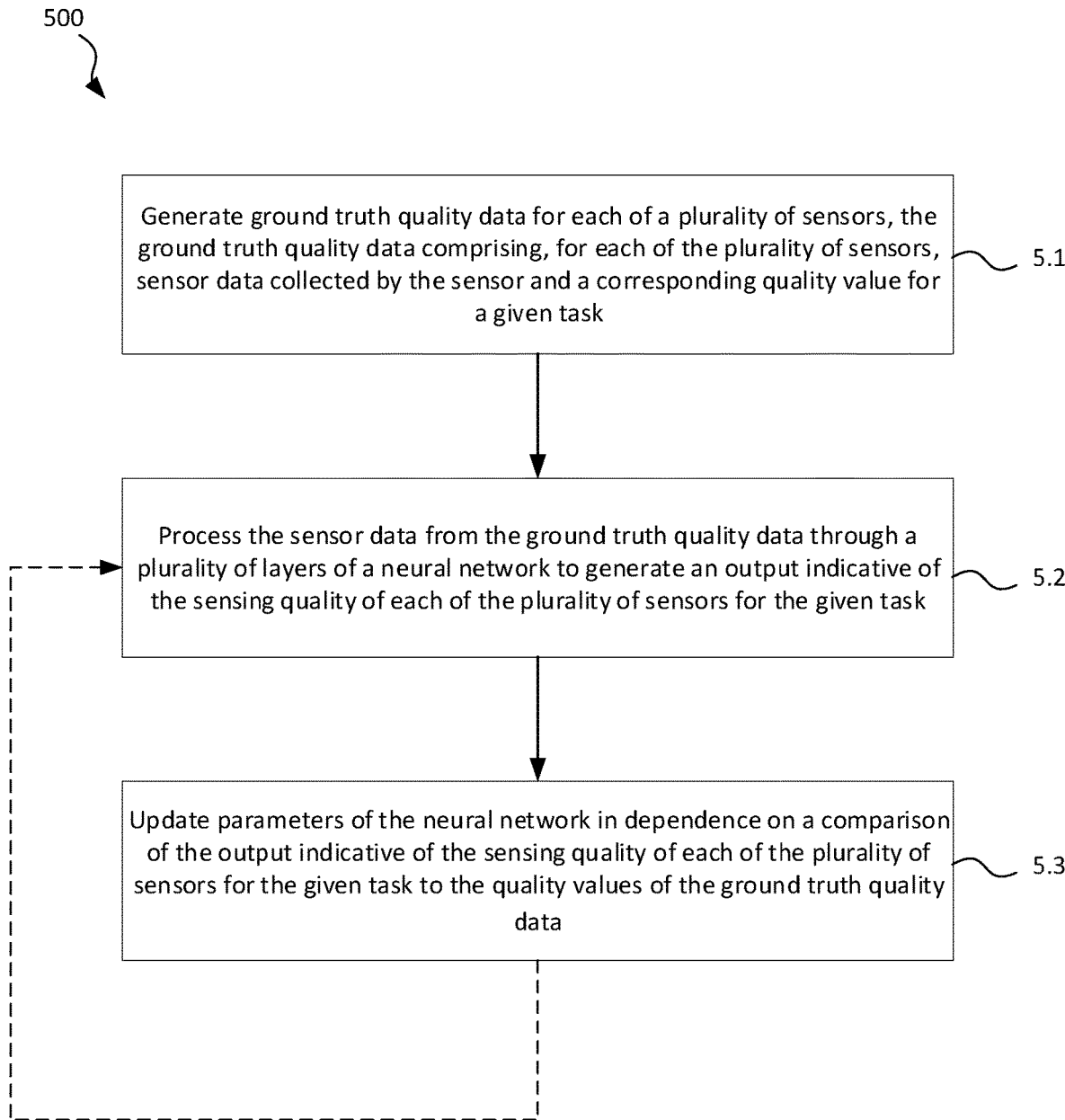

Generate ground truth quality data for each of a plurality of sensors, the ground truth quality data comprising, for each of the plurality of sensors, sensor data collected by the sensor and a corresponding quality value for a given task
5.1

Process the sensor data from the ground truth quality data through a plurality of layers of a neural network to generate an output indicative of the sensing quality of each of the plurality of sensors for the given task
5.2

Update parameters of the neural network in dependence on a comparison of the output indicative of the sensing quality of each of the plurality of sensors for the given task to the quality values of the ground truth quality data
5.3

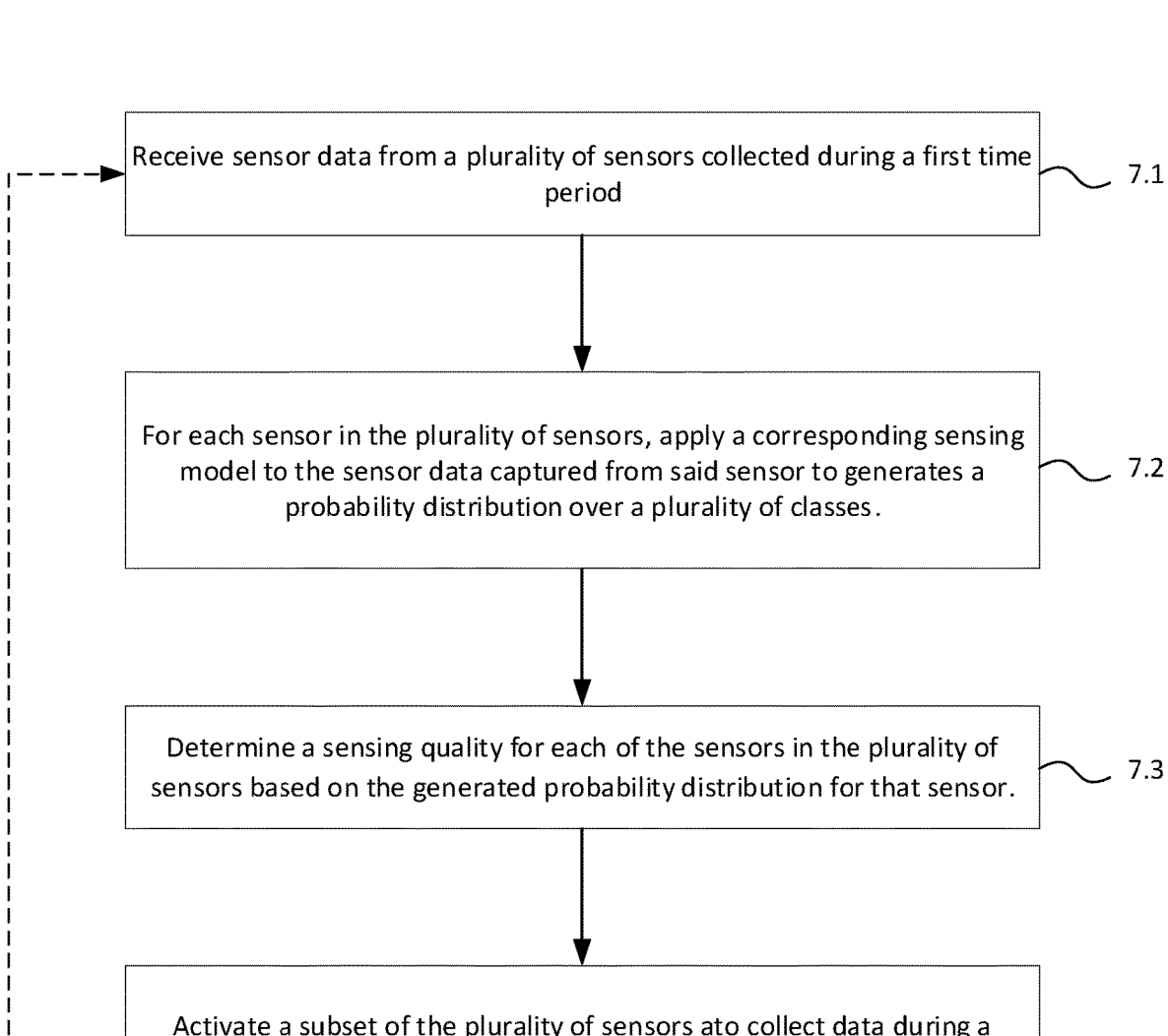

Receive sensor data from a plurality of sensors collected during a first time period — 7.1

For each sensor in the plurality of sensors, apply a corresponding sensing model to the sensor data captured from said sensor to generates a probability distribution over a plurality of classes. — 7.2

Determine a sensing quality for each of the sensors in the plurality of sensors based on the generated probability distribution for that sensor. — 7.3

Activate a subset of the plurality of sensors ato collect data during a second time period based on the determined sensing quality of each of the plurality of sensors for the given task. — 7.4

Figure 7

RUNTIME ASSESSMENT OF SENSORS

FIELD

This relates to the field of sensor evaluation. More particularly, this relates to the use of sensor evaluation in a multi-sensor environment.

BACKGROUND

The increasing availability of multiple sensory devices on or near a human body has opened brand new opportunities to leverage redundant sensory signals for the development of powerful human sensing applications. For instance, personal-scale sensory inferences with time-varying signals (e.g., motion, audio etc.) can be performed individually on each of a plurality of devices (e.g. a smartphone, a smartwatch, and even an earbud), each offering unique sensor quality, model accuracy, runtime behaviour and usage dynamics. At execution time, however, it is incredibly challenging to assess and compare these characteristics to select the best device for accurate and resource-efficient sensory inferences.

Moreover, the presence of redundant sensors is not only limited to human sensing scenarios; in industrial automation systems, the deployment of redundant sensors is widely used to ensure reliability of the system. For example, in a future where self-driving cars are the norm, several redundant sensors will ensure high levels of safety and reliability. Sensors outside and inside the car will work together with wearable sensors on the driver's body to monitor the conditions of the road, of the car and the psychophysical status of the driver.

SUMMARY

In a first aspect, this specification describes apparatus comprising: at least one processor; and at least one memory including computer program code. The at least one memory and the computer program code are configured to, with the at least one processor, cause the apparatus at least to perform: receive sensor data from a plurality of sensors collected during a first time period; process the received sensor data through a plurality of layers of a neural network to generate an output indicative of the sensing quality of each of the plurality of sensors for a task; and cause a subset of the plurality of sensors to collect data during a second time period based on the output indicative of the suitability of each of the plurality of sensors for the task.

The neural network may comprise: a plurality of input sub-networks, each input sub-network configured to receive as input sensor data from one of the plurality of sensors and to extract one or more features from said input sensor data; and a plurality of fully connected layers, the plurality of fully connected layers configured to process features extracted by the plurality of input sub-networks and generate the output indicative of the suitability of each of the plurality of sensors for the given task. Each of the input sub-networks may comprise one or more convolutional layers. Two or more of the input sub-networks may have identical weights.

The output indicative of the suitability of each of the plurality of sensors for the task may be a set of binary values, each binary value associated with one of the sensors in the plurality of sensors and indicative of the suitability of said one of the sensors for performing the task.

The first period of time may be a fixed period of time. The first period of time may be between about 1 and 5 seconds, for example between 2 and 4 seconds.

The second period of time may be a fixed period of time, for example between 1 and 60 seconds, such as between 20 and 50 seconds. The second period of time may be a variable period of time dependent on a threshold quality of the sensor data collected at the second period of time.

The method performed by the apparatus may be iterated after the second period of time has elapsed.

The apparatus may be: a user device; a smartphone; a smartwatch; a smart earbud; or a tablet device. The apparatus may be a remote server.

The task may comprise one or more of: human activity recognition; hot-word recognition; health monitoring; environmental monitoring; physiological monitoring; and/or exercise monitoring.

The plurality of sensors may comprise one or more of: an accelerometer; a microphone; a gyroscope; a thermometer; a magnetometer; a positioning sensor; a light sensor; a pedometer; a barometer; a heart rate sensor; and/or a humidity sensor.

In a further aspect, this specification describes a system comprising: a plurality of user devices, each user device comprising one or more sensors; and any of apparatus described herein.

In a further aspect, this specification describes a method comprising: receiving sensor data from a plurality of sensors collected during a first time period; processing the received sensor data through a plurality of layers of a neural network to generate an output indicative of the sensing quality of each of the plurality of sensors for a task; and causing a subset/one or more of the plurality of sensors to collect data during a second time period based on the output indicative of the suitability of each of the plurality of sensors for the task.

The neural network may comprise: a plurality of input sub-networks, each input sub-network configured to receive as input sensor data from one of the plurality of sensors and to extract one or more features from said input sensor data; a plurality of fully connected layers, the plurality of fully connected layers configured to process features extracted by the plurality of input sub-networks and generate the output indicative of the suitability of each of the plurality of sensors for the task. Each of the input sub-networks may comprise one or more convolutional layers. Each of the input sub-networks may have identical weights.

The output indicative of the suitability of each of the plurality of sensors for the task may be a set of binary values, each binary value associated with one of the sensors in the plurality of sensors and indicative of the suitability of said one of the sensors for performing the task.

The first period of time may be a fixed period of time. The first period of time may be between about 1 and 5 seconds, for example between 2 and 4 seconds.

The second period of time may be a fixed period of time, for example between 1 and 60 seconds, such as between 20 and 50 seconds. The second period of time may be a variable period of time dependent on a threshold quality of the sensor data collected at the second period of time. The second period of time may a variable period of time dependent on a threshold quality of the sensor data collected at the second period of time.

The method may be iterated after the second period of time has elapsed.

The method may be performed on: a user device; a smartphone; a smartwatch; a smart earbud; or a tablet device. The method may be performed on a remote server.

The task may comprise one or more of: human activity recognition; hot-word recognition; health monitoring; environmental monitoring; exercise monitoring; and/or physiological monitoring.

The plurality of sensors may comprise one or more of: an accelerometer; a microphone; a gyroscope; a thermometer; a magnetometer; a positioning sensor; a light sensor; a pedometer; a barometer; a heart rate sensor; and/or a humidity sensor.

In a further aspect, this specification describes a method comprising: generating ground truth quality data for each of a plurality of sensors, the ground truth quality data comprising, for each of the plurality of sensors, sensor data collected by the sensor and a corresponding quality value for a given task; processing the sensor data from the ground truth quality data through a plurality of layers of a neural network to generate an output indicative of the sensing quality of each of the plurality of sensors for the given task; and updating weights of the neural network in dependence on a comparison of the output indicative of the sensing quality of each of the plurality of sensors for the given task to the quality values of the ground truth quality data.

Generating ground truth quality data for each of a plurality of sensors may comprise, for one or more sensors in the plurality of sensors: applying a sensing model to sensor data collected from a sensor in the plurality of sensors to generate a predicted class for said sensor data; and generating a ground truth quality in dependence on the comparison of the predicted class for said sensor data to a known class for said sensor data.

The operations of processing the sensor data from the ground truth quality data and updating weights of the neural network may be iterated until a threshold condition is met.

The comparison of the output indicative of the sensing quality of each of the plurality of sensors for the given task to the quality values of the ground truth quality data may be performed using a loss function. For example, a cross entropy loss function may be used. The updates to the weights may be determined by applying an optimisation procedure to the loss function.

The neural network may comprise: a plurality of input sub-networks, each input sub-network configured to receive as input sensor data from one of the plurality of sensors and to extract one or more features from said input sensor data; a plurality of fully connected layers, the plurality of fully connected layers configured to process features extracted by the plurality of input sub-networks and generate the output indicative of the suitability of each of the plurality of sensors for the given task. Each of the input sub-networks may comprise one or more convolutional layers. Two or more of the input sub-networks may have identical weights. All of the sub-networks may have identical weights.

The output indicative of the suitability of each of the plurality of sensors for the task may be a set of binary values, each binary value associated with one of the sensors in the plurality of sensors and indicative of the suitability of said one of the sensors for performing the given task.

In a further aspect, this specification describes computer readable instructions which, when executed by computing apparatus, cause the computing apparatus to perform one or more of the methods disclosed herein.

In a further aspect, this specification describes apparatus configured to perform one or more of the methods disclosed herein.

In a further aspect, this specification describes apparatus comprising means for performing one or more of the methods disclosed herein.

In a further aspect, this specification describes a non-transitory computer readable medium comprising program instructions for causing an apparatus to perform one or more of the methods disclosed herein.

BRIEF DESCRIPTION OF THE DRAWINGS

FIG. 3 shows a flow diagram of an example method of runtime assessment of sensors using a neural network;

FIG. 5 shows a flow diagram of an example method of training a neural network for runtime assessment of sensors;

FIG. 7 shows a flow diagram of an example method of runtime assessment of sensors using a heuristic approach;

DETAILED DESCRIPTION

In contrast to single-device environments, multi-device environments have the feature of sensing redundancy. In other words, there are multiple sensors available to compute inferences about users and their environment. This is enabled by the fact that most of these devices today share a common set of core sensors such as an accelerometer, a gyroscope, or a microphone and thereby offering redundant sensory signals to quantify physical events. For example, activity tracking can be done individually on a smartphone, a smartwatch, and even an earbud. Similarly, audio can be recognised by selectively using a microphone on one of these devices or a nearby Internet of Things (IoT) device for audio-sensing tasks at any given context.

This scenario raises two main challenges:

(a) the system ends up computing redundant inferences thereby consuming precious battery power on all the devices. As modern inference models based on deep learning can be computationally very expensive, this redundant computation has a significant impact on overall energy usage.

(b) it is not straightforward to combine the individual device inferences and present a unified view to the user. For example, due to their different positions on the body, a smartphone may infer that a user is 'climbing stairs' while the smartwatch may infer that user is 'running'.

In general, different devices offer varying sensor quality, model accuracy, spatiotemporal coverage, runtime behaviour, and usage dynamics. Moreover, these characteristics change over time due to several factors including device variability, e.g., hardware and software heterogeneity, compute budget, energy budget, etc. and temporal or context variability, e.g., device placement, the distance between a user and a device, a user's surrounding situation, etc.

Figure 1:
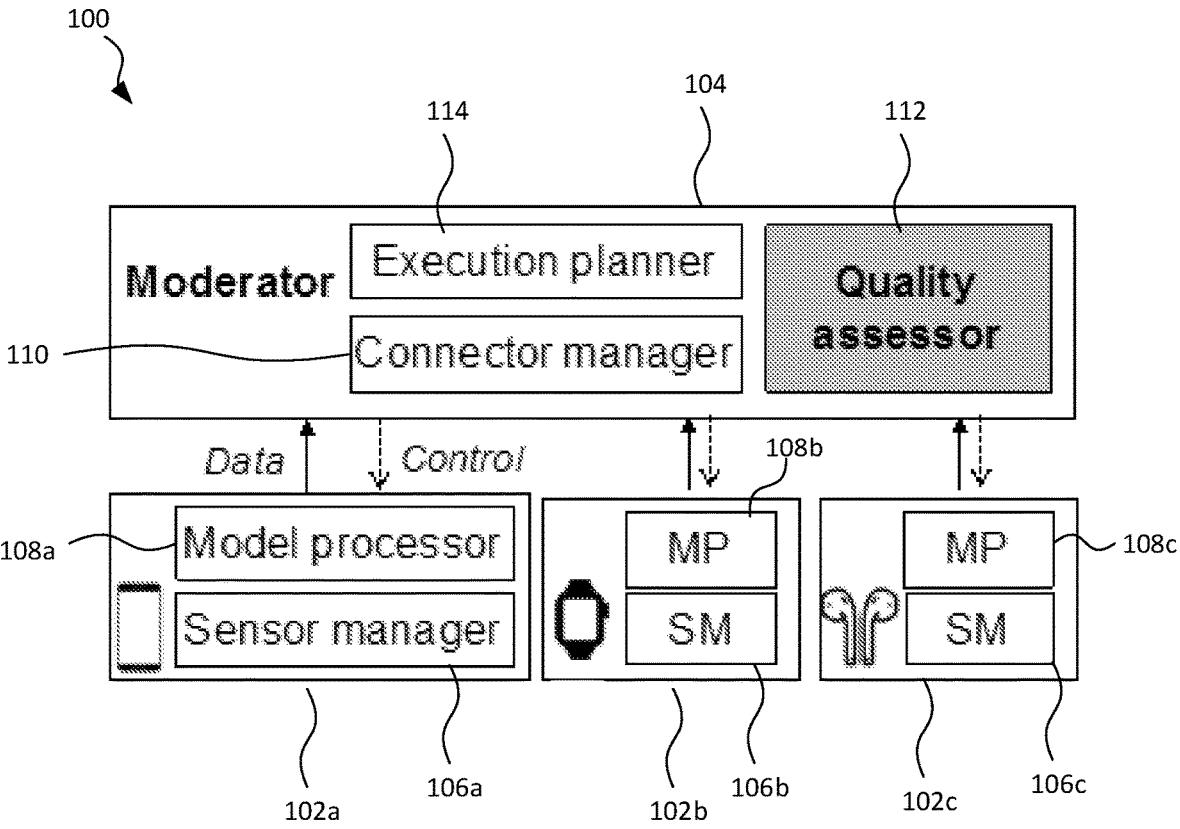
FIG. 1 shows an example embodiment of a system for runtime assessment of sensors.

FIG. 1 shows an embodiment of a system 100 for runtime assessment of sensors. The system 100 actively interplays between multiple devices 102, each containing one or more sensors/sensing devices and respective sensing models 108 (also referred to herein as a "model processor"), to dynamically select the one or more best sensors/sensing devices for a recognition/sensing task at hand. The best performing device may dynamically change throughout execution of the given task even though the availability of sensors/sensor devices may not change.

The primary aim of quality-based device selection is to assess and compare the quality of sensor data from each device at run-time. As used herein, quality is tied to the accuracy of a sensing task—in other words, given N sensor streams, the sensor stream which provides the highest accuracy of the inference task at hand is said to have the best quality. The redundancy in sensors means that, with carefully orchestrated scheduling, sensing tasks can be supported longer by selectively using different devices at different times. Since each device is different and offers different runtime characteristics and sensing performances, better recognition accuracy can be achieved by selecting the best device for the task at hand at each inference instance.

The system 100 (also referred to herein as a multi-device environment) comprises a plurality of user devices 102, each comprising one or more sensors. In the example shown, the user devices 102 comprises a smartphone 102a, a smartwatch 102b and a set of headphones 102c, though one or more other devices, such as a computer tablet, a personal communication device, a still/video camera, an IoT device, an antenna, a transmitter, a receiver, a processor, a memory unit, a vehicle sensor, an IMU (Inertial Measurement Unit), a global navigation satellite system (GNSS) sensor, a single sensor device or the like, or any combination thereof may alternatively or additionally be used. Together, the sensors available to the system form a plurality of sensors. The system 100 further comprises an apparatus 104 (also referred to herein as a "moderator") configured to receive sensor data from the plurality of user devices 102, and to analyse the sensor data to determine which of the plurality of sensors should be activated when performing a given task. In the example shown, the apparatus 104 comprises a smartphone, such 102a, though one or more other devices, such any user device 102, a personal computer, a server, an edge server, a cloud computing unit, a wireless communication access point, an engine control module (ECM) or the like, or any combination thereof may alternatively or additionally be used. The apparatus 104 coordinates the collection of sensor data for the multi-device environment.

Each device 102 comprises one or more sensors/sensing devices (not shown). The sensors of each device 102 may be controlled by a sensor manager 106 residing on the device 102. Each device 102 may further comprise a sensing model 108 configured to implement one or more task-specific sensing models on the sensor data. For example, in the case of a Human Activity Recognition (HAR) task, there is an HAR inference model on all HAR enabled devices that a user is carrying, such as a smartphone, a smartwatch and a smart earbud.

The set of available sensors in the system is denoted herein as $\{D^i\}$, where $D^i$ is the $i^{th}$ sensor/sensing device.

Each sensor may be associated with a sensing model, $M^i$, where $M^i$ is the sensing model $i^{th}$ sensor/sensing device. At a time, t, the sensors generate a set of sensor data $$S_t = \{S_t^i\},$$

where $$S_t^i$$

is sensor data collected from the $i^{th}$ sensor/sensing device at time t. Additionally, each sensor may have one or more sensing models M.

The plurality of sensors in the system 100 may comprise one or more sets of redundant sensors (i.e. sets of sensors that measure the same, or equivalent, variables). The redundant sensors may reside on different devices 102 (i.e. two or more of the user devices 102 comprise a sensor that measure the same, or equivalent, variables). As illustrative examples, the plurality of sensors may comprise one or more of: a set of accelerometers; a set of microphones; a set of gyroscopes; a set of thermometers; a set of magnetometers; a set of positioning sensors (such as satellite positioning sensors); a set of light sensors; a set of pedometers; a set of barometers; a set of heart rate sensors; and/or a set of humidity sensors.

The system 100 further comprises an apparatus 104 (also referred to herein as a "moderator") configured to receive sensor data from the plurality of user devices 102, and to analyse the sensor data to determine which of the plurality of sensors should be activated to perform the task at hand. The apparatus 104 comprises at least one processor and at least one memory, the memory comprising computer program code that, when executed, causes the apparatus to perform one or more of the methods disclosed herein.

The apparatus 104 may comprise a connection manager 110. The connector manager 110 manages the registered connectors in multi-device environments and detects the available devices at runtime. The connection manager may interact with a network interface in the apparatus 104 to connect to the devices 102.

The apparatus 104 may comprise a quality assessor 112. The quality assessor 112 is configured to assess the sensing quality of available sensors/sensing devices at runtime using a quality assessment model. Examples of quality assessment models are described below in relation to FIGS. 3 to 7.

The apparatus 104 may further comprise an execution planner 114. The execution planner 114 is configured to receive the sensing quality of the available sensors/sensing devices from the quality assessor 112 and determine an execution plan for the task at hand. Determining the execution plan comprises selecting which of the available sensors/sensing devices to use for the task based on the sensing quality of the available sensors/sensing devices. Additionally, the execution plan also may also comprise determination of time intervals for an execution duty cycle 212, an assessment window 202, a sensing window, and an execution window 210. Once the execution plan is determined by the execution planner 114, the apparatus 104 manages the execution of the sensor and sensing models.

The apparatus 104 may be a "master device" separate from the set of user devices 102, such as shown in FIG. 1. In other embodiments, the apparatus 104 may be, or may reside in, one or more or the user devices 102. In some embodiments, where multiple user devices 102 are capable of implementing/hosting the apparatus 104, the user device acting as the master device can be dynamically chosen from among the multiple user devices 102 based on a one or more predetermined criteria. For example, the master device may be chosen based on the availability of computing resources (e.g. memory, bandwidth, processing power etc.) on each of the user devices 102 or the available apparatuses 104. Alternatively or additionally, the master device can be dynamically chosen based on a selected task, such as running or walking, and/or related context information, such as awake, asleep, at home, or at work. In some embodiments, the apparatus 104 may be a remote server, for example operating in the cloud.

Figure 2A:
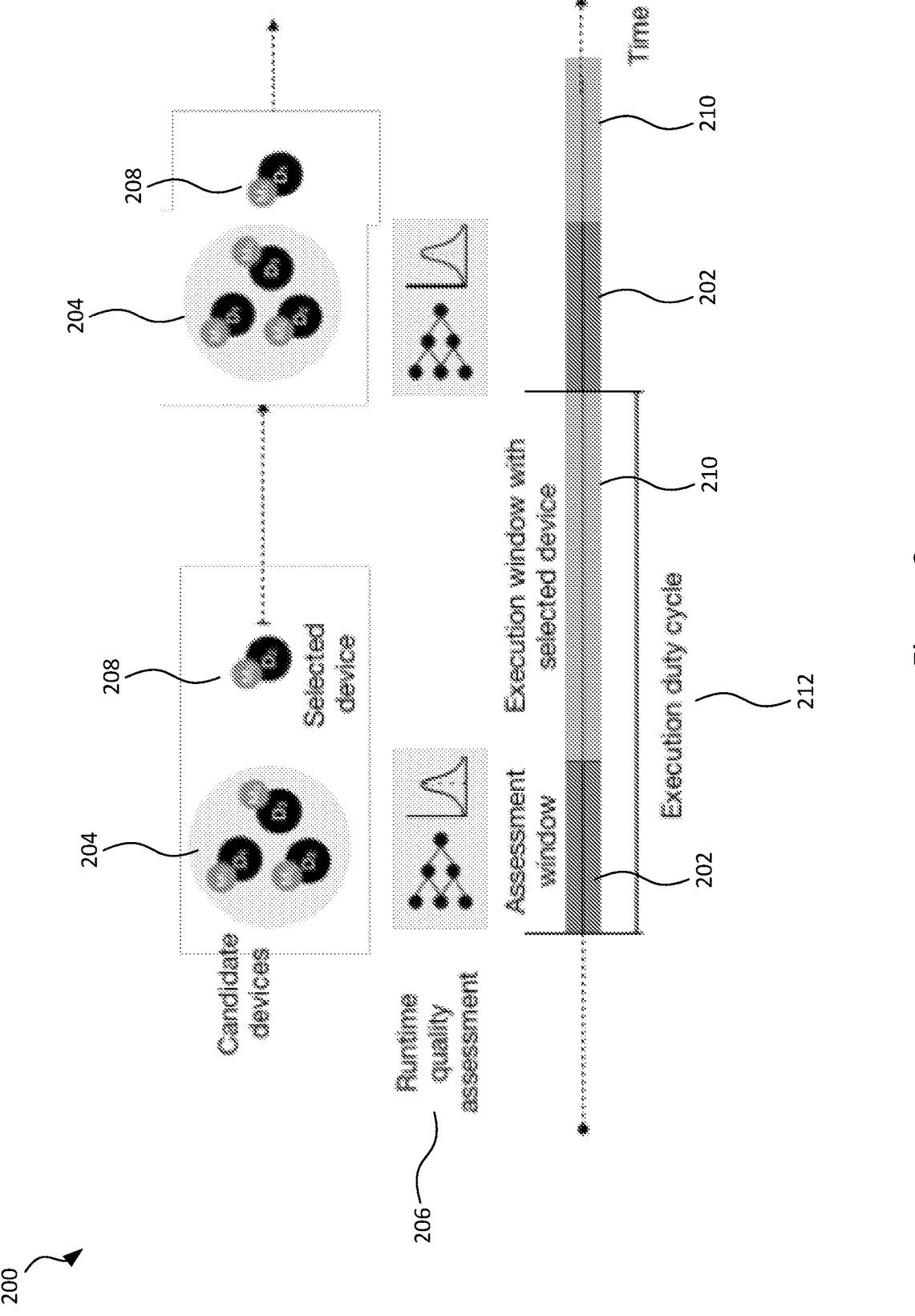
FIG. 2a shows an overview of an example method of runtime assessment of sensors.
Figure 2B:
FIG. 2b shows a further overview of an example method of runtime assessment of sensors.

FIGS. 2a and 2b show overviews of methods 200 of runtime assessment of sensors. FIG. 2a shows a learning based approach that utilises a neural network. FIG. 2b shows both a learning based approach and a heuristic approach. The methods may, for example, be performed in the system of FIG. 1.

During a first period of time 202 (also referred to herein as an "assessment window") sensor data is collected from the plurality of sensors/sensing devices 204 in the multi-device environment. The collection of sensor data during the first time period may, for example, be managed by the quality assessor 112 or the execution planner. The first time period 202 may be a fixed period of time. For example, the first period 202 of time may last between one and five seconds. The length of the first period 202 of time may be variable, for example the first period of time may be dependent on one or more of: the task/s being performed by the sensors/sensing devices; the type of sensor data being collected; the amount of sensor data that is collected; the number of redundant sensors in the plurality of sensors/sensing devices. In embodiments where the first period of time 202 is variable, there may be an upper threshold to the first period of time 202. For example, the upper threshold may last between one and five seconds.

During the first time period 202, one or more quality assessment models 206 are applied to the collected sensor data to estimate the sensing quality of the available sensors/sensing devices and/or the associated sensing models (M or SM) 204 in the given task and/or context. The one or more quality assessment models may be applied to the raw sensor data collected by the available sensors/sensing devices 204 and/or the associated sensing models to processed features from the sensor data (i.e. to pre-processed sensor data, for example sensor data that has been processed by sensing models 214). In some embodiments, contextual data is also supplied to the one or more quality assessment models for use in determining the quality of the sensors/sensing devices and the sensing models.

In some embodiments, the quality assessment models 206 may comprise one or more learned models 206a, such as pre-trained neural networks. Examples of the use of pre-trained neural networks as quality assessment models are described in further detail below in relation to FIGS. 3-6. Alternatively or additionally, the quality assessment models 206 may comprise one or more heuristic models 206b. Examples of the use of heuristic models as quality assessment models are described in further detail below in relation to FIG. 7.

The quality assessment models 206 may each be tailored for a particular task. For example, a library of quality assessment models 206 may be provided, each tailored to a different task, with the one or more quality assessment models 206 used in the first time period 202 being selected based on the current task/tasks being executed. The library may contain both heuristic models 206b and learned models 206a, with the particular type of model used being based on the current task. Contextual data, indicative of the current context of the user, may also be used to select the one or more quality assessment models 206.

Based on the output of the quality assessment model 206, one or more sensors/sensing devices 208 and/or one or more sensing models (SM) are selected for use in a current sensing task. The output (for example, a quality score that can be e.g. a vector, a binary variable and/or continuous variable) is used to select the device and/or the sensing model with the best data quality for the underlying inference task—in other words, a device and/or a sensing model is selected which is the most likely to provide the best accuracy for the current sensing task. Alternatively, the output (for example, the quality score) is used to select one or more devices and/or one or more sensing models with the best or adequate data quality combination, such as accuracy, for the underlying inference task, so that they the most likely to provide the best accuracy for the current sensing task. A specific sensor/sensing device 208 may have one or more related sensing models (M or SM), wherein each sensing model may be defined for a specific task and/or context.

Thereafter, the one or more selected sensors/sensing devices 208 are used for a second period of time 210 (also referred to herein as the "execution window") to collect sensor data and/or for computing inferences relating to the task. In some embodiments, the sensors/sensing devices that are not selected are deactivated.

The second period of time 210 may last for a predetermined amount of time. For example, the predetermined amount of time may be between 1 and 60 seconds, preferably between 5 and 60 seconds. In some embodiments, the second period of time may last until the task is complete. In some embodiments, the second period of time may be variable, and depend on, for example, amount and/or complexity of sensor data collected during the second period of time 210. For example, if the sensor data collected during the second period of time falls below a predetermined quality threshold, the second period of time may be ended, and a further assessment window started. Further, the second period of time 210 may be divided to one or more "Sense" and "Sensing Model" (SM) periods, wherein during the "Sense" period sensor data is collected from the selected one or more devices 204, and during the "Sensing Model" period the collected sensor data is analysed with the selected one or more sensing models. The "Sense" and "Sensing Model" (SM) periods may last for a predetermined amount of time, or they may last until the task is complete. Additionally, the "Sense" and "Sensing Model" period may be variable, and depend on, for example, amount and/or complexity of sensor data collected. Further, if the sensor data collected during the "Sense" period falls below a predetermined data quality threshold, the second period of time 210 may be ended, and a further assessment window 202 is started. Further, if the quality of the "Sensing Model" during the related period falls below a predetermined sensing quality threshold, the second period of time 210 may be ended, and a further assessment window 202 is started.

After each execution duty cycle 212 (i.e. assessment window+execution window), the process of assessing the sensing quality and selecting the best device may be performed again. In other words, the cycle 212 of assessment window followed by execution window may be iterated. The execution duty cycle 212 is a continuous process.

FIG. 3 shows a flow diagram of an example method 300 of runtime assessment of sensors using a neural network. The method may be performed by the apparatus 104 of FIG. 1. In some embodiments, the method 300 is performed on a user device 102, such as a smartphone, smartwatch or other mobile computing device. In some embodiments, the method 300 is performed remotely, for example in the cloud.

At operation 3.1, sensor data $S_t$ is received from a plurality of sensors during a first time period. The receipt of sensor data $S_t$ may be managed by the connector manager 110 of apparatus 104. The sensor data originates from one or more sensors residing on a plurality of user devices. At least some of the received sensor data may be pre-processed sensor data. At least some of the received sensor data may be raw sensor data. The first period of time (or assessment window) may be a fixed period of time. The fixed period of time may be between about 1 second and 5 seconds.

At operation 3.2, the received sensor data $S_t$ is processed through a plurality of layers of a neural network to generate output indicative of a sensing quality of each of the plurality of sensors and their associated sensing models for a task. Operation 3.2 may, for example, be performed by the quality assessor 112 of apparatus 104. The task comprises a task that uses sensor data in some way. The task may comprise one or more of: human activity recognition; hot-word recognition; health monitoring; environmental monitoring; physiological monitoring; exercise monitoring, industrial process monitoring, apparatus process monitoring, communication system monitoring, vehicle functions monitoring, or the like, in any combination thereof. In a complex task, that requires activation of two or more sensors, the quality assessor 112 assesses combined accuracy of the two or more sensors.

The input $S_t$ to the neural network is a k-tuple of the form $$S_t = \langle S_t^1, S_t^2, S_t^3 \ \dots \ S_t^k \rangle,$$

representing the sensor data from k sensors captured at time t/a segment of sensor data from k sensors at time t.

The output may be one or more quality scores. The quality score for each sensor, i, may be a binary variable, $q^i$, that indicates whether or not that sensor and/or its associated sensing model is suitable for the current task (e.g. a score of 1 for sensor i indicates that sensor i is suitable for the given task, whereas a score of 0 for sensor i indicates that sensor i is not suitable for the given task). Alternatively, the quality score may a continuous variable. Additionally, the quality score may describe quality of two or more sensors indicating, whether or not the two or more sensors and/or their associated sensing model are together suitable for the current task.

An example of the structure of a neural network that can be used for this operation is provided below with reference to FIG. 4

At operation 3.3, one or more of the plurality of sensors are activated to collect data during a second time period based on the output indicative of a sensing quality of each of the plurality of sensors for the given task. The execution manager 114 of the apparatus 104 may cause the one or more sensors to be activated. The second period of time may be a fixed period of time. For example, the second period of time may last between about 1 second and about 60 seconds, preferably between about 5 seconds and 60 seconds. In some embodiments, the duty cycle lasts about 10 seconds, with an assessment time of about 1 second.

In some embodiments, further data in addition to the output indicative of a sensing quality of each of the plurality of sensors for the task may be used to select the subset of sensors to activate. For example, resource metrics relating to the devices on which the sensors are located can be used. Additional information about the current status of the devices, such as remaining battery or CPU and memory load, may additionally be used as inputs for the device selection procedure. This way the subset of sensors device may be selected not only based on the signal quality of its sensors, but also based on the current resources available.

In some embodiments, the execution planner 114 can allow the definition of policies to prioritise accuracy or energy efficiency. These policies may be updated/switched dynamically based on the current status of the system to aloe for adaptation as the system evolves. For example, as the overall energy available in the devices starts depleting, longer duty cycle windows could be adopted. With the availability resources metrics from the devices it should be possible to realise and adaptive execution planner which distributes the computation according to the desired policy.

The sensor data collected during the second time is used to perform/in performance of the task at hand. For example, audio data collected by a microphone is used to perform hot-word detection. Accelerometer data may be used to determine/classify a current user activity. Many other examples are possible.

Figure 4:
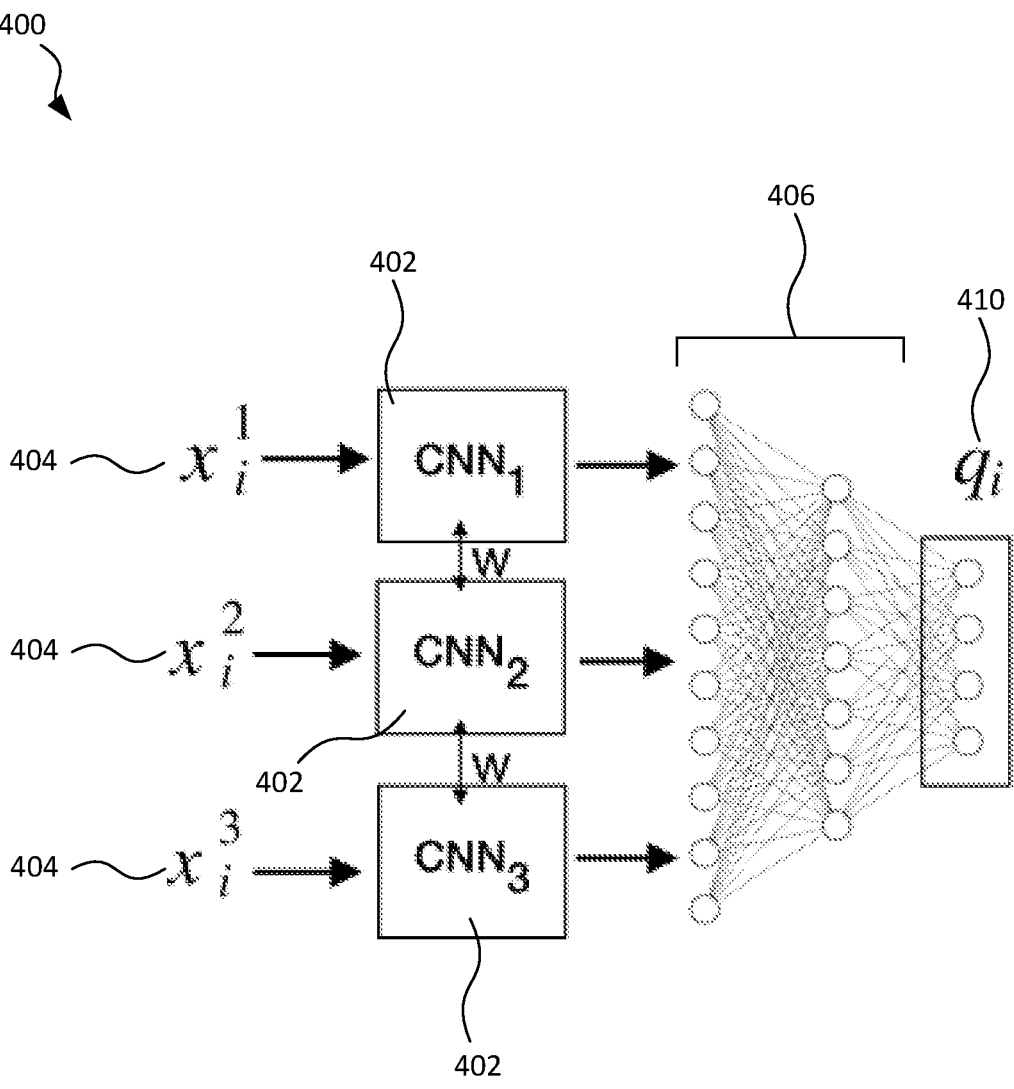
FIG. 4 shows an example of a neural network structure for use in runtime assessment of sensors.

FIG. 4 shows an example of a neural network structure 400 for use in the method of FIG. 3. The neural network 400 is a neural network configured to process input sensor data to generate an output indicative of a sensing quality of each of the plurality of sensors for a given task. The neural network 400 comprises a plurality of layers of nodes, each node associated with one or more parameters. The parameters of each node of the neural network 400 may comprise one or more weights and/or biases. The nodes take as input one or more outputs of nodes in the previous layer, or the input sensor data. The one or more outputs of nodes in the previous layer are used by the node to generate an activation value using an activation function and the parameters of the neural network. The parameters of the neural network may be determined using a training process, as described below in relation to FIG. 5

The neural network 400 comprises a plurality of input sub-networks 402 (also referred to herein as "towers"), each input sub-network 402 configured to receive as input sensor data 404 from one of the plurality of sensors and to extract one or more features from said input sensor data. Each tower 402 receives sensor data $x^i_t$ from a different sensor/sensing device and extracts higher order features One or more of the input subnetworks 402 may be identical (i.e. have the same structure and weights, w), and may therefore the neural network 400 may be referred to as a "Siamese neural network". In some embodiments, input sub-networks 402 relating to sensors of the same type are identical. For example, the input neural networks 402 relating to accelerometer data from multiple devices may use weight-sharing identical sub-networks 402 to extract higher-order features. By sharing the weights across multiple sub-networks, the size of the model can be reduced, thus making it more feasible to run on devices with limited runtime memory.

In some embodiments, the input sub-networks 402 may comprise one or more convolutional layers. The input sub-networks 402 may further comprise one or more pooling layers. For example, the input sub-networks 402 may comprise three 2D convolution and pooling layers for feature extraction. However, greater or fewer convolutional layers may be used. The input subnetworks 402 may further comprise a global average pooling layer.

The neural network 400 further comprises a plurality of fully connected layers 406, the plurality of fully connected layers 406 configured to process features extracted by the plurality of input sub-networks and generate the output 410 indicative of the suitability of each of the plurality of sensors for the given task, $q_i$. The plurality of fully connected layers 406 is configured to compare the features extracted by the input sub-networks 402 to determine which sensors to use for the collection if sensor data in the second time period. The outputs of the input subnetworks 402 may be concatenated and input into the fully connected layers. The final layer of the network may have a sigmoid activation function.

In some embodiments, the neural network 400 further comprises one or more attention blocks/attention mechanisms. These can allow the model to automatically cope with the absence of sensor data in an input by weighting the internal features accordingly to the sensor data available at each moment in time. It provides additional flexibility once the model has been trained.

FIG. 5 shows a flow diagram of an example method 500 of training a neural network, which may, in some embodiments, be managed by the quality assessor 112, for runtime assessment of sensors. In some embodiments, the method 500 is performed on a user device 104. In some embodiments, the method 500 is performed remotely, for example in the cloud. The method is an example of a supervised learning technique, though unsupervised learning may alternatively be used, where the model is trained without reference to labelled ground truth data. The training method may be performed by one of the devices/apparatus of the system 100. Alternatively, it may be performed remotely, for example in the cloud.

At operation 5.1, ground truth quality data is generated for each of a plurality of sensors, the ground truth quality data comprising, for each of the plurality of sensors, sensor data collected by the sensor and a corresponding quality value for a given task.

The ground truth dataset for the training of a neural network comprises one or more k-tuples of the form $$X = \{X_1, \ X_2, \ X_3 \ \dots \ X_K\}$$

where $$X_k(k = 1 \ \dots \ K)$$

denotes the sensor dataset from sensor/sensing device $D_k$. Each sensor dataset comprises one or more samples, $$X_k^t,$$

taken at time t. $\gamma_t$ denotes the ground truth class for the sample at time t. Note that if the k sensor streams are time-synchronized, they will share the same ground truth at time t. The ground truth dataset further comprises a ground truth quality vector $q_t$ (where $|q_t|=k$) which denotes the quality of each of the k sensor inputs.

Examples of generating ground truth quality data are described below with reference to FIG. 6.

At operation 5.2, the sensor data from the ground truth quality data is processed through a plurality of layers of a neural network to generate an output indicative of the sensing quality of each of the plurality of sensors for the given task. The training input $X_t$ to the neural network at each iteration is a k-tuple of the form $$X_t = \langle X_t^1, X_t^2, x_t^3 \ \dots \ X_t^k \rangle,$$

representing ground truth sensor data from k sensors captured at time t. The neural network may be the same as any of the neural networks described above in relation to FIG. 3 or 4.

At operation 5.3, parameters of the neural network are updated in dependence on a comparison of the output indicative of the sensing quality of each of the plurality of sensors for the given task to the quality values of the ground truth quality data. A loss/objective function may be used to compare the output indicative of the sensing quality of each of the plurality of sensors for the given task to the quality values of the ground truth quality data. Examples of loss/objective functions that may be used include, but are not limited to, cross entropy losses. An optimisation procedure may be applied to the loss/objective function to determine the parameter updates. For example, a gradient descent/ascent algorithm may be used to determine the parameter updates.

Operations 5.2 and 5.3 may be iterated until a threshold condition is met. Examples of threshold conditions comprise: a threshold number of iterations; one or more convergence criteria; a threshold amount of the ground truth quality data being processed; and/or a threshold accuracy on a test dataset being achieved.

Figure 6:
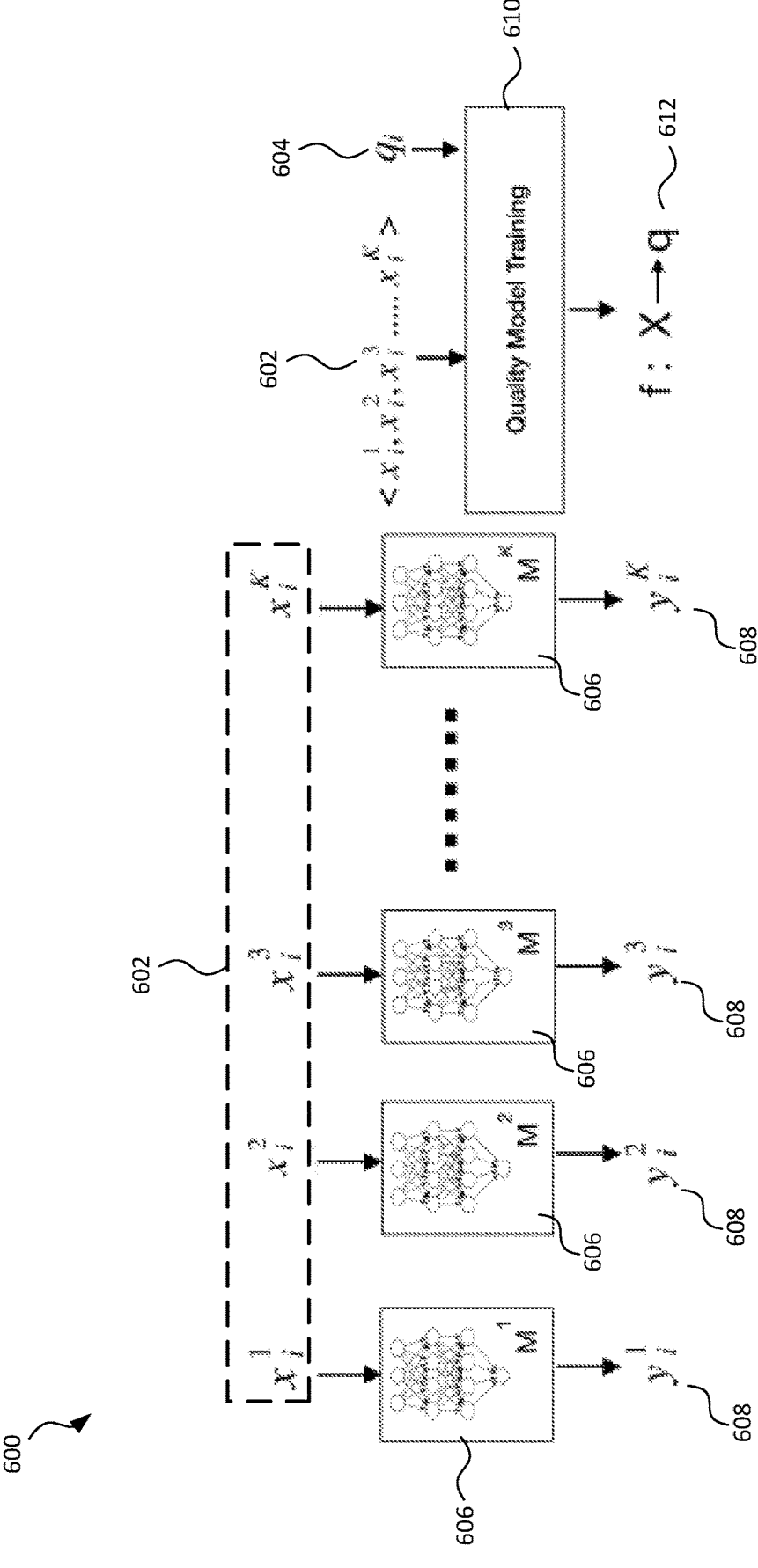
FIG. 6 shows an overview of an example method of generating ground truth quality data.

FIG. 6 shows an overview of an example method 600 of generating ground truth quality data, which may, in some embodiments, be managed by the quality assessor 112. The ground truth quality data comprises a labelled dataset, $p(X_t, q_t)$, where $X_t$ is a k-tuple of aligned sensor data from k devices 602. $q_t$ is a k-dimensional vector representing quality ground truth 604, with $$q_t^k$$

being the quality of the $k^{th}$ sensor/sensing device at time t. In other words, $$q_t = \langle q_t^1, q_t^2, q_t^3 \ \dots \ q_t^k \rangle.$$

$\dots q_t^k\rangle$. In some embodiments, the labelled dataset may also comprise ground truth classes, $\gamma_t$, that label a k-tuple $X_t$ 602 as relating to a particular class (e.g. labelling the sensor data as relating to a particular activity). The ground truth classes may be discrete labels. Alternatively, the ground truth classes may be continuous numerical labels.

In some embodiments the quality ground truth 604 may be a vector/set of binary variables, $q^i \in \{0,1\}$. The binary variables may indicate that a particular sensor/sensing device is suitable for the given task. In some embodiments, score of 1 for sensor i indicates that sensor i is suitable for the given task, whereas a score of 0 for sensor i indicates that sensor i is not suitable for the given task. For example, if there are three sensors/sensing devices $D^1$, $D^2$ and $D^3$, then $$q = [1, 1, 0]$$

indicates that $D^1$ and $D^2$ are suitable for the task, and that $D^3$ is not suitable for the task.

In some embodiments, the quality ground truth 604 may be a vector/set of continuous variables. The continuous variables may lie in some predefined range, $q^i \in [a,b]$. For example, the continuous variables may lie in the range [0,1], with higher numbers indicating a higher quality of sensor (i.e. more suitable for the given task).

As discussed above, the quality of a device is the suitability of a device to a given sensing task. In other words, the quality represents the ability of a sensor data $X_t$ 602 make accurate predictions for the task at hand (for example, to accurately recognise a current user activity). The quality ground truth 604 can be generated using pre-trained device-specific sensing models 606, $M_k$, which predict an output label 608, $$y_t^k,$$

given sensor data $$X_t^k, \text{ i.e. } M_k: X_f^k \rightarrow y_t^k.$$

As an illustrative example, there could be an HAR model for device which predicts activity classes such as running, walking, sitting from accelerometer data collected on the device. The output label 608, $$y_t^k$$

may be a discrete label. Alternatively, the output label 608 may be a continuous numerical label.

For each set of sensor data 602 at time t, $X_t$, the corresponding models 606, $M_k$, are applied to the data, $$X_t^k,$$

to generate predictions 608, $$y_t^k.$$

Each prediction 608

$$y_t^k$$

is compared with a corresponding ground truth class at step t, $\gamma_t$, to determine the ground truth quality 604, $$q_t^k.$$

In some embodiments, the ground truth quality 604 may be given by:

$$q_t^k = \begin{cases} 1 & \text{if } q_t^k = \gamma_t \\ 0 & \text{if } q_t^k \neq \gamma_t \end{cases}$$

In other words, if the prediction from sensing device $D^k$ matches the ground truth at time t, the data from this device has good quality and $$q_t^k$$

is set to 1. However, other methods may alternatively be used. For example a score representing how close the prediction $$y_t^k$$

is to the ground truth class, $\gamma_t$, may be generated.

The generated quality ground truth and corresponding sensor data can then be used to train 610 the neural network quality assessment model to predict 612 quality scores from input sensor data, as describe above in relation to FIG. 5.

FIG. 7 shows a flow diagram of an example method 700 of runtime assessment of sensors using a heuristic approach, which may, in some embodiments, be managed by the quality assessor 112. The method can be used as an alternative to the neural network based method described above.

A further method of assess sensing quality is to leverage confidence values reported from a sensing classifier. Examples include probabilities from probabilistic classifiers, such as naive Bayes and logistic regression, probabilities from a softmax layer in neural networks, and distance to a hyperplane boundary in a Support Vector Machine (SVM). Confidence values represent how confident a classifier is on the inference output from a given input data. These can therefore be used as a measure of sensing quality. For example, a probability value can represent the probability of given sensor data being a member of each of class in a set of possible classes. The highest probability outputted by a model can then be used as a measure of quality It is not always straightforward to use confidence values as measure of sensing quality. For example, while modern neural networks provide exceptional accuracy, it is reported that their probabilities are often not well calibrated, especially in multi-class classification. That is, for given sensor data, the relative order of the probabilities is sufficiently accurate to select the most probable class, but the absolute probability value does not represent the expected accuracy well. In other words, just by looking at the output probabilities of two classifiers for a given task, it cannot always be judged which one is more accurate (or confident) in its predictions.

To address this issue, a number of techniques have been proposed in machine learning literature to calibrate the outputs of the classifiers and make them resemble the actual probability distribution of the training data. As an example, Platt scaling may be used for calibrating the inference models. Platt scaling may be used because of its ease of implementation and good performance with neural networks.

To quantify sensing quality from calibrated probabilities, uncertainty sampling strategies can be used to measure uncertainty of instances, i.e., how uncertain a given instance is to be labelled. Calibrated probabilities of sensor data, $$S_t^i,$$

determined from the corresponding sensor model, $M_i$, can be defined as $$P_t^i = \{P_{t,k}^i\}$$

where $P_{t,k}^i$ is a probability value that $$S_t^i$$

belongs to class $C_k$, where C is a set of classes, $\{C_k\}$. A heuristic method can be used based on this definition.

At operation 7.1, sensor data is received from a plurality of sensors during a first time period 202. The sensor data originates from sensors residing on a plurality of user devices 102. At least some of the received sensor data may be pre-processed sensor data. At least some of the received sensor data may be raw sensor data.

At operation 7.2, for each sensor in the plurality of sensors, a corresponding sensing model, $M_k$, is applied to the sensor data captured from said sensor. Each sensing model generates a probability distribution over a plurality of classes, the probability distribution representative of the probability of the corresponding sensor data belonging to each of those classes, $$P_t^i.$$

At operation 7.3, a sensing quality is determined for each of the sensors in the plurality of sensors based on the generated probability distribution for that sensor. The sensing quality given an input set of sensor data from sensor i, $S_t^i$, with corresponding sensing model $M_i$, may be denoted $$Q(S_t^i, M_i).$$

In some embodiments, a highest confidence method is used to determine the sensing quality. The sensing quality is taken to be the highest confidence. That is, the quality function is defined as the probability of the most likely label of given sensor data, i.e., $$Q(S_t^i, M_i) = \max(P_t^i).$$

In some embodiments, a highest margin sampling method is used to determine the sensing quality. Highest margin sampling measures the certainty by taking a difference between probabilities of the two most likely classes. More specifically, the quality function, Q is defined as the difference between the highest and second highest probability, i.e., $$Q(S_t^i, M_i) = \max(P_t^i) - \max 2nd(P_t^i),$$

where max2nd is a function that outputs the second maximum value.

In some embodiments, an entropy based method is used to measure certainty/uncertainty. The concept of entropy has been proposed in the domain of information theory, but is also widely used to measure uncertainty or impurity in machine learning. Here, the distribution of an instance with lower entropy can be considered more confident than that with higher entropy. The quality can be given by the reciprocal of the entropy of the distribution. The quality function, Q, can be defined as:

$$Q(S_t^i, M_i) = \frac{-1}{\sum_k P_{t,k}^i \log P_{t,k}^i}.$$

At operation 7.4, a subset of the plurality of sensors are activated to collect data during a second time period 210 based on the determined sensing quality of each of the plurality of sensors for the given task. Sensors having the highest quality measure can be selected, and used to collect sensor data for the given task during the execution window.

The sensor data collected during the second time is used to perform/in performance of the given task. For example, audio data collected by a microphone is used to perform hotword detection.

Figure 8:
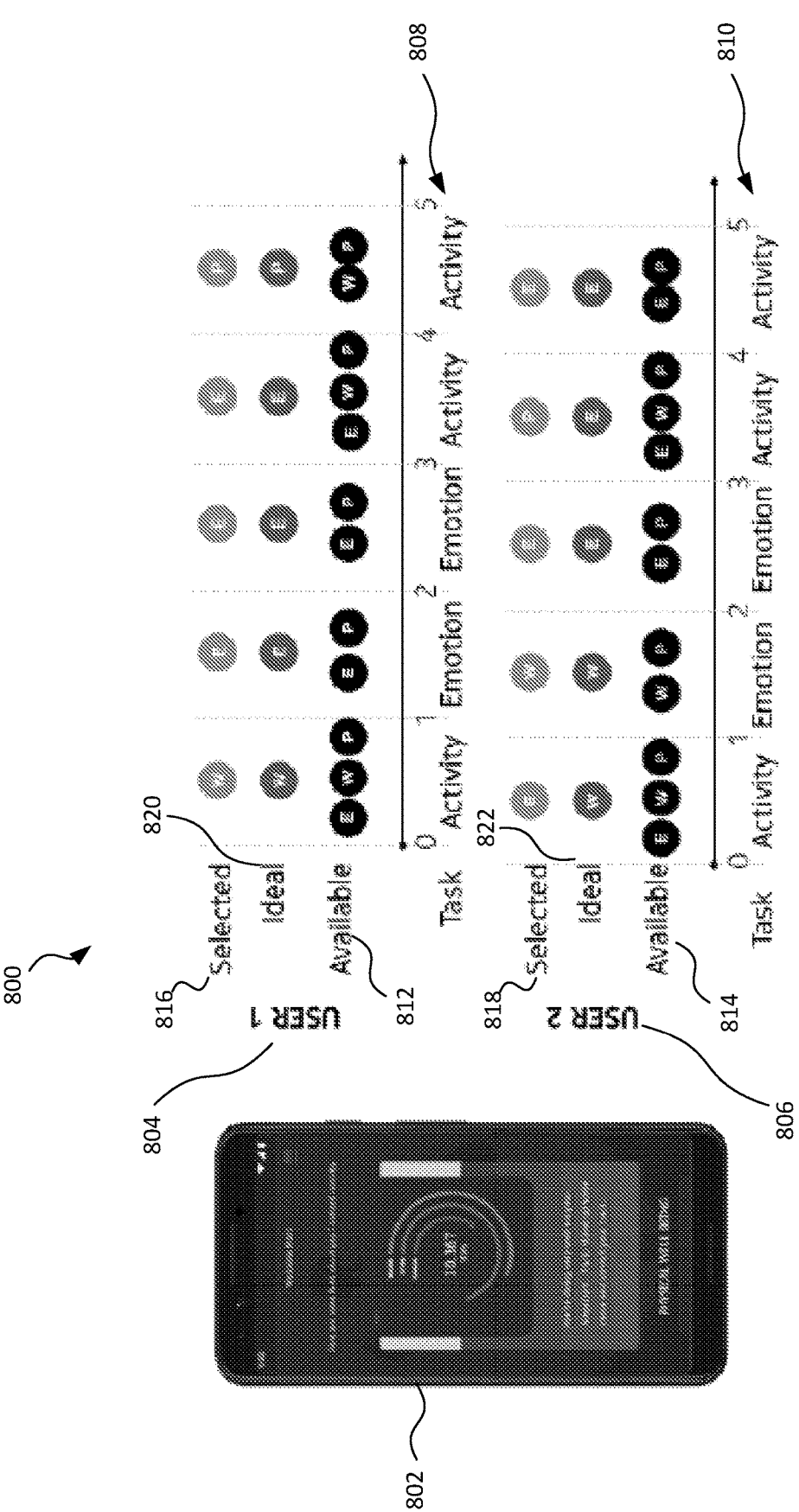
FIG. 8 shows an example of an application of the method of runtime assessment of sensors to a well-being management application.

FIG. 8 shows an example of the results 800 of an application of the method of runtime assessment of sensors to a well-being management application. The example is only one of many examples to which the systems, methods and apparatus disclosed herein can be applied. The application comprises a wellbeing monitoring application that captures motion activities using an IMU (e.g. walking, standing, and sitting) and emotional states using a microphone. These attributes are then summarised and provided to a user, for example with a visual and conversational feedback of their physical and mental well-being. The application is shown as being performed on a smartphone 802, but can alternatively be performed on any capable apparatus, such as a smart watch, tablet etc.

The smartphone 802 (or alternative apparatus) can connect to multiple sensory devices, for example over a wireless network protocol (e.g. BLE and/or Wi-Fi). The sensory devices may provide, for example, motion and audio data.

Such sensing devices may, for example, include smartphones 802 (labelled "p" in FIG. 8), smart watches (labelled "w" in FIG. 8), and smart earbuds (labelled "w" in FIG. 8). Each of the sensing devices may comprise one or more of: an accelerometer, a gyroscope, and/or a microphone.

The application uses the runtime quality assessment and execution planning capabilities to selectively use one or more of the sensing devices and their corresponding sensing models to track the wellbeing attributes. The wellbeing attributes comprise an activity attribute and an emotion attribute.

The results of the runtime assessment are provided for two users 804, 806. As series of five duty cycles 808, 810 are shown for each user 804, 806. During each duty cycle, assessment of the available sensors 812, 814 for one of the available tasks (in this example, either activity assessment or emotion assessment) is performed to select one or more of the available sensors to perform the task. In the example shown, the smart earbuds, smartwatch and smartphone are each capable of sensing data required for the activity assessment, while only the smart earphones and smartphone are capable of sensing data required for the emotion assessment.

The selected sensor 816, 818 is then used to collect sensor data for performing the corresponding task during the rest of the duty cycle. Note that during different duty cycles, the sensor data collected during the assessment phase may be different and/or the context may change, so a different sensing device may be selected for the same task during different duty cycles. For example, in the example shown for the first user, the smart watch is selected to collect data for activity assessment during the first duty cycle, but the smart earbuds and smartphone are selected to collect sensor data for activity assessment during the fourth and fifth duty cycles respectively.

An ideal selection 820, 822 for each duty cycle is shown for the purpose of comparison.

Figure 9:
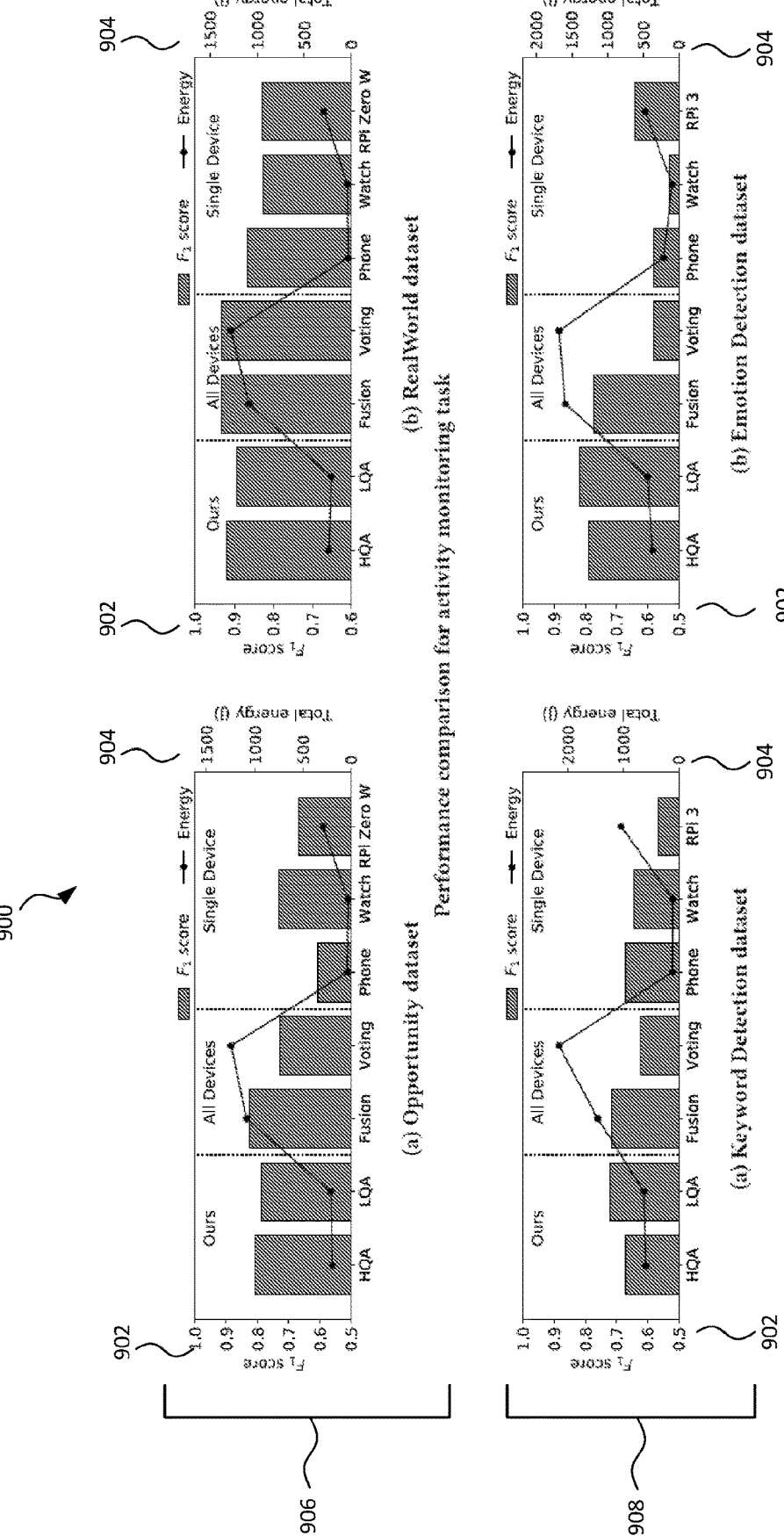
FIG. 9 shows graphs of examples of the performance of runtime assessment methods disclosed herein against several baselines.

FIG. 9 shows graphs 900 of examples of the performance of runtime assessment methods disclosed herein against several baselines.

Each graph 900 shows a recognition accuracy score 902 (the "F1 score") as a bar chart and the total energy consumption 904 for the task over one hour as a line graph. Two example tasks are shown: an activity monitoring task 906 and an audio understanding task 908. For each activity, the results using two datasets are shown. Three devices are used in performing each task: a smartphone, a smartwatch and a computing device (e.g. RPi Zero W) for the activity monitoring and a smartphone, a smartwatch and a computing device (e.g. RPi 3) for the audio understanding task.

Three baselines are shown. One baseline is the "single device" baseline, which represents the traditional practice in sensing, wherein each device makes sensing inferences separately without any collaboration with other devices. Note that each model is trained for each device using the data from the very device. The total energy consumption for this baseline is the sum of energy consumption of the three devices. Another baseline is the "voting" baseline. For the voting baseline, at any given point in time, the inferences are computed from each device individually, and the output that has been predicted by the majority of the devices is selected. Another baseline is the "fusion" baseline. In the fusion baseline, a trained model is used that takes as input the sensor streams from all devices and outputs the predicted activity.

As illustrated in the graphs 900, the learning based quality assessment (LQA) and heuristic based quality assessment (HQA) consume less energy than the other baseline methods, while providing better accuracy than the single device baseline, and comparable accuracy to or better accuracy than the fusion and voting baselines.

Figure 10:
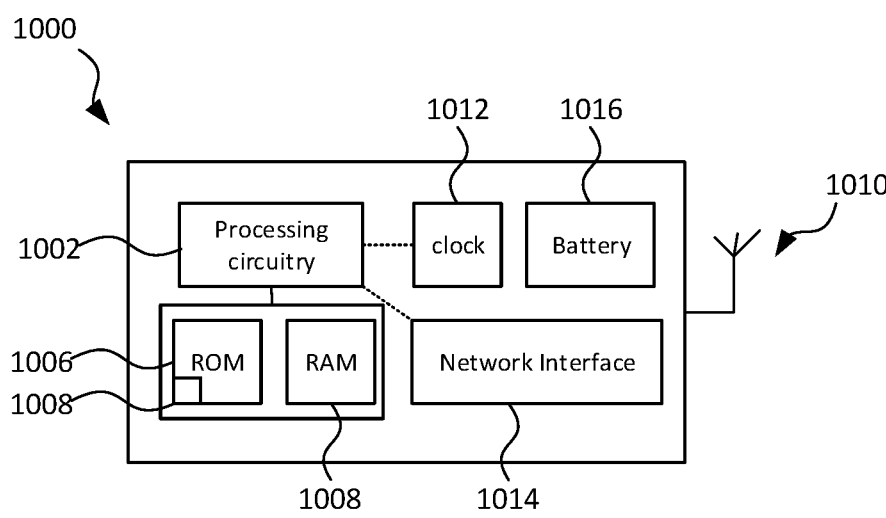
FIG. 10 shows a schematic representation of an example of the electronics system of apparatus or user devices.

FIG. 10 shows a schematic representation of an example of the electronics system 1000 of apparatus 104 or user devices 102.

The electronics system 1000 comprises a processor arrangement 1002. The processor arrangement 1002 and other hardware components may be connected via a system bus (not shown). Each hardware component may be connected to the system bus either directly or via an interface. A power supply is arranged to provide power to the electronics system.

The processor arrangement 1002 controls operation of the other hardware components of the electronics system. The processor arrangement 1002 may be one or more integrated circuits of any kind. The processor arrangement 1002 may for instance be one or more general purpose processors. It may be a single core device or a multiple core device. The processor arrangement 1002 may be a central processing unit (CPU) or a general processing unit (GPU). Alternatively, it may be a more specialist unit, for instance a RISC processor or programmable hardware with embedded firmware. Multiple processors 1002 may be included. The processor arrangement 1002 may be termed processing means.

The electronics system comprises one or more working or volatile memories 1004. The processor arrangement 1002 may access the volatile memory 1004 in order to process data and may control the storage of data in memory. The volatile memory 1004 may be a RAM of any type, for example Static RAM (SRAM), Dynamic RAM (DRAM), or it may be Flash memory. Multiple volatile memories 1004 may be included, but are omitted from the Figure.

The electronics system comprises one or more non-volatile memories 1006. The non-volatile memory 1006 stores a set of operation instructions 1008 for controlling the normal operation of the processor arrangement 1002. The non-volatile memory 1006 may be a memory of any kind such as a Read Only Memory (ROM), a Flash memory or a magnetic drive memory. Other non-volatile memories may be included, but are omitted from the Figure.

The processor arrangement 1002 operates under the control of the operating instructions 1008. The operating instructions 1008 may comprise code (i.e. drivers) relating to the hardware components of the electronics system, as well as code relating to the basic operation of the apparatus. The operating instructions 1008 may also cause activation of one or more software modules stored in the non-volatile memory 1006. Generally speaking, the processor arrangement 1002 executes one or more instructions of the operating instructions 1008, which are stored permanently or semi-permanently in the non-volatile memory 1006, using the volatile memory 1004 temporarily to store data generated during execution of the operating instructions.

The processor arrangement 1002, the volatile memory 1004 and the non-volatile memory 1006 may be provided as separate integrated circuit chips connected by an off-chip bus, or they may be provided on a single integrated circuit chip. The processor arrangement 1002, the volatile memory 1004 and the non-volatile memory 1006 may be provided as a microcontroller.

The electronics system further comprises one or more receivers and/or transmitters 1010. The receiver and/or transmitter 1010 are operable to receive and/or transmit electromagnetic signals.

The electronics system 1000 comprises a clock 1012. The clock 1012 may be a clock crystal, for example, a quartz crystal oscillator. The clock 1012 may be a separate component to the processor arrangement 1002 which is configured to provide a clock signal to the processor arrangement 1002. The processor arrangement 1002 may be configured to provide a real time clock based on the signal from the clock 1012. Alternatively, the clock 1012 may be a clock crystal which is provide on a single integrated circuit chip with the processor arrangement 1002.

In some embodiments, the electronics system comprises one or more wireless and/or wired network interfaces 1014. The network interfaces 1014 facilitate the connection of the apparatus to one or more computer networks and the bi-directional exchange of information between the apparatus 104/user devices 102 and other members of the networks. These networks may include the Internet, a Local Area Network (LAN), Personal Area Network (PAN), Body Area Network (BAN), Wireless Body Area Network (WBAN), Body Sensor Network (BSN), Medical Body Area Network (MBAN), Vehicle Area Network (VAN), a vehicle bus network, or any other network required by the apparatus 104/user devices 102 to communicate with each other. The network interfaces 1014 comprise a network interface controller, such as an Ethernet adaptor, a Wi-Fi adaptor and/or a Bluetooth adaptor. The network interfaces 1014 are associated with one or more network addresses for identifying the apparatus on the network. The one or more network addresses may be in the form of an IP address, a MAC address, and/or an IPX address. The network interfaces 1014 may be connected to the receiver/transmitter 1010 in order to connect to wireless networks.

The electronics system may be provided with a battery 1016 to supply power to the apparatus 104/user device 102.

Embodiments may be implemented in software, hardware, application logic or a combination of software, hardware and application logic. The software, application logic and/or hardware may reside on memory, or any computer media. In example embodiments, the application logic, software or an instruction set is maintained on any one of various conventional computer-readable media. In the context of this document, a "memory" or "computer-readable medium" may be any media or means that can contain, store, communicate, propagate or transport the instructions for use by or in connection with an instruction execution system, apparatus, or device, such as a computer.

Reference to, where relevant, "computer-readable storage medium", "computer program product", "tangibly embodied computer program" etc., or a "processor" or "processing circuitry" etc. should be understood to encompass not only computers having differing architectures such as single/multi-processor architectures and sequencers/parallel architectures, but also specialised circuits such as field programmable gate arrays FPGA, application specify circuits ASIC, signal processing devices and other devices. References to computer program, instructions, code etc. should be understood to express software for a programmable processor firmware such as the programmable content of a hardware device as instructions for a processor or configured or configuration settings for a fixed function device, gate array, programmable logic device, etc.

As used in this specification, the term 'circuitry' refers to all of the following: (a) hardware-only circuit implementations (such as implementations in only analogue and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of 'circuitry' applies to all uses of this term in this specification, including in any claims. As a further example, as used in this specification, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in server, a cellular network device, or other network device.

Figure 11:
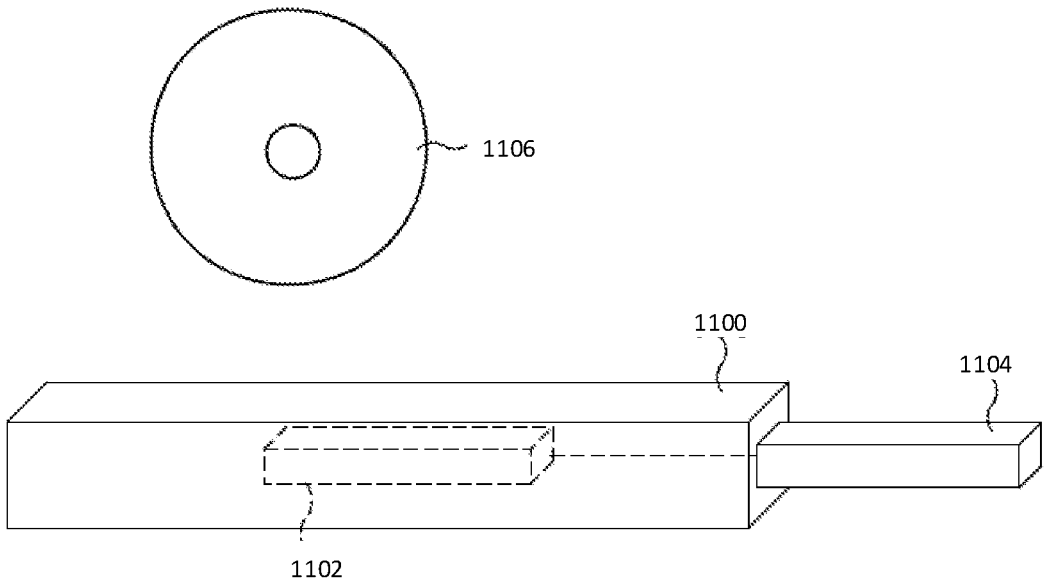
FIG. 11 shows examples of computer readable media/computer program products.

FIG. 11 shows examples of computer readable media/computer program products 1100, 1106. In some examples, the computer readable medium 1100 is in the form of a portable memory device (such as a "memory stick"). In some examples, the computer readable medium comprises a computer readable disk 1106, such as a CD-ROM or DVD. Many other examples are possible. The computer program product 1100 comprises a memory 1102 containing computer readable instructions that may provide the logic and routines that enables a computing apparatus to perform the functionality described herein. It may also comprise an interface 1104, such as a USB interface for example, for communicating with the computing apparatus. In some examples, the computer readable medium/computer program product may be non-transitory.

Although various aspects of the methods and apparatuses described herein are set out in the independent claims, other aspects may comprise other combinations of features from the described embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims. The extent of protection is defined by the following claims, with due account being taken of any element which is equivalent to an element specified in the claims.

The invention claimed is:

1. An apparatus comprising at least one processor; and at least one memory including computer program code; the at least one memory and the computer program code configured to, with the at least one processor, cause the apparatus at least to perform:

generate ground truth quality data for a plurality of sensors, the ground truth quality data comprising sensor data collected by the plurality of the sensors and a corresponding quality value for an inference task, wherein the corresponding quality value indicates an accuracy of the inference task using the sensor data;

process the sensor data from the ground truth quality data through a plurality of layers of a neural network to generate an output indicative of sensing quality of the plurality of the sensors for the inference task;

update weights of the neural network in dependence on a comparison of the output indicative of the sensing quality of the plurality of sensors to the quality values of the ground truth quality data;

select one or more of the plurality of the sensors based on the output indicative of the sensing quality of the one or more of the plurality of the sensors for the inference task;

cause the one or more of the plurality of the sensors to collect data during a second time period for the inference task; and apply a sensing model of the selected one or more sensors to the collected data to generate a probability distribution over a plurality of classes for the inference task.

2. The apparatus of claim 1, wherein the generating of the ground truth quality data for the plurality of the sensors comprises, for one or more sensors in the plurality of the sensors:

apply a sensing model to sensor data collected from a sensor in the plurality of the sensors to generate a predicted class for said sensor data; and generate the ground truth quality data in dependence on the comparison of the predicted class for said sensor data to a known class for said sensor data.

3. The apparatus of claim 1, wherein operations of the processing of the sensor data from the ground truth quality data and the updating of the weights of the neural network are iterated until a threshold condition is met.

4. The apparatus of claim 1, wherein the comparison of the output indicative of the sensing quality of the plurality of the sensors for the inference task to the quality values of the ground truth quality data is performed using a loss function.

5. The apparatus of claim 4, wherein the weights are determined by applying an optimization procedure to the loss function.

6. The apparatus of claim 1, wherein the neural network comprises:

a plurality of input sub-networks, each input sub-network configured to receive as input sensor data from one of the plurality of the sensors and to extract one or more features from said input sensor data;

a plurality of fully connected layers configured to process features extracted by the plurality of the input sub-networks and generate the output indicative of the suitability of each of the plurality of the sensors for the inference task.

7. The apparatus of claim 6, wherein two or more of the input sub-networks have identical weights.

8. The apparatus of claim 1, wherein the output indicative of the suitability of the plurality of the sensors for the inference task is a set of binary values, each binary value associated with one of the sensors in the plurality of the sensors and indicative of the suitability of said one of the sensors for performing the inference task.

9. The apparatus of claim 1, wherein the apparatus is a user device, a smartphone, a smartwatch, a smart earbud, a tablet device or a server.

10. The apparatus of claim 1, wherein the plurality of the sensors are implemented in one or more of the user device, the smartphone, the smartwatch, the smart earbud, the tablet device or the server.

11. The apparatus of claim 1, wherein the inference task comprises one or more of human activity recognition, hotword recognition, health monitoring, environmental monitoring, physiological monitoring, and/or exercise monitoring.

12. A method comprising:

generating ground truth quality data for a plurality of sensors, the ground truth quality data comprising sensor data collected by the plurality of the sensors and a corresponding quality value for an inference task, wherein the corresponding quality value indicates an accuracy of the inference task using the sensor data;

processing the sensor data from the ground truth quality data through a plurality of layers of a neural network to generate an output indicative of sensing quality of the plurality of the sensors for the inference task;

updating weights of the neural network in dependence on a comparison of the output indicative of the sensing quality of the plurality of sensors to the quality values of the ground truth quality data;

selecting one or more of the plurality of the sensors based on the output indicative of the sensing quality of the one or more of the plurality of the sensors for the inference task;

causing the one or more of the plurality of the sensors to collect data during a second time period for the inference task; and applying a sensing model of the selected one or more sensors to the collected data to generate a probability distribution over a plurality of classes for the inference task.

13. The method of claim 12, wherein the generating of the ground truth quality data for the plurality of the sensors comprises, for one or more sensors in the plurality of the sensors:

applying a sensing model to sensor data collected from a sensor in the plurality of the sensors to generate a predicted class for said sensor data; and generating the ground truth quality data in dependence on the comparison of the predicted class for said sensor data to a known class for said sensor data.

14. The method of claim 12, wherein operations of the processing of the sensor data from the ground truth quality data and the updating of the weights of the neural network are iterated until a threshold condition is met.

15. The method of claim 12, wherein the comparison of the output indicative of the sensing quality of the plurality of the sensors for the inference task to the quality values of the ground truth quality data is performed using a loss function.

16. The method of claim 15, wherein the weights are determined by applying an optimization procedure to the loss function.

17. The method of claim 12, wherein the neural network comprises:

a plurality of input sub-networks, each input sub-network configured to receive as input sensor data from one of the plurality of the sensors and to extract one or more features from said input sensor data;

a plurality of fully connected layers configured to process features extracted by the plurality of the input sub-networks and generate the output indicative of the suitability of each of the plurality of the sensors for the inference task.

18. A non-transitory computer readable medium comprising program instructions for causing an apparatus to perform:

generating ground truth quality data for a plurality of sensors, the ground truth quality data comprising sensor data collected by the plurality of the sensors and a corresponding quality value for an inference task, wherein the corresponding quality value indicates an accuracy of the inference task using the sensor data;

processing the sensor data from the ground truth quality data through a plurality of layers of a neural network to generate an output indicative of sensing quality of the plurality of the sensors for the inference task;

updating weights of the neural network in dependence on a comparison of the output indicative of the sensing quality of the plurality of sensors to the quality values of the ground truth quality data;

selecting one or more of the plurality of the sensors based on the output indicative of the sensing quality of the one or more of the plurality of the sensors for the inference task;

causing the one or more of the plurality of the sensors to collect data during a second time period for the inference task; and applying a sensing model of the selected one or more sensors to the collected data to generate a probability distribution over a plurality of classes for the inference task.

19. The apparatus of claim 1, wherein a sensor of the plurality of sensors is associated with a respective sensor model.

\* \* \* \* \*